(12) United States Patent
Kendrick et al.

(10) Patent No.: US 6,623,774 B2
(45) Date of Patent: Sep. 23, 2003

(54) PREPARATION AND STABILIZATION OF FOOD-GRADE MARINE OILS

(75) Inventors: Andrew Kendrick, Hatton (GB); Neil Macfarlane, Elloughton (GB)

(73) Assignee: Roche Vitamins Inc., Parsippany, NJ (US)

( * ) Notice: Subject to any disclaimer, the term of this patent is extended or adjusted under 35 U.S.C. 154(b) by 135 days.

(21) Appl. No.: 10/194,178

(22) Filed: Apr. 5, 2001

(65) Prior Publication Data

US 2003/0161918 A1 Aug. 28, 2003

Related U.S. Application Data

(63) Continuation of application No. 09/608,401, filed on Jun. 30, 2000, now abandoned, which is a continuation of application No. 09/434,186, filed on Nov. 4, 1999.

(30) Foreign Application Priority Data

Nov. 4, 1998 (EP) ............................................. 98120888
Sep. 17, 1999 (EP) ............................................. 99118426

(51) Int. Cl.$^7$ ............................. A23D 9/06; A23D 9/02
(52) U.S. Cl. .................... 426/330.6; 426/417; 426/541; 426/601
(58) Field of Search .............................. 426/330.6, 417, 426/601, 541; 436/161; 95/82

(56) References Cited

U.S. PATENT DOCUMENTS

| | | | | | |
|---|---|---|---|---|---|
| 4,525,306 | A | * | 6/1985 | Yajima | 426/93 |
| 4,877,635 | A | * | 10/1989 | Todd, Jr. | 426/542 |
| 5,006,281 | A | * | 4/1991 | Rubin et al. | |
| 5,023,100 | A | * | 6/1991 | Chang et al. | 426/601 |
| 5,077,069 | A | * | 12/1991 | Chang et al. | 426/330.6 |
| 5,084,289 | A | * | 1/1992 | Shin et al. | 426/330.6 |
| 5,855,944 | A | * | 1/1999 | Koschinski et al. | 426/541 |

OTHER PUBLICATIONS

Karahadian, C. 1989. Evaluation of Compounds Contributing Characterizing Fishy Flavors in Fish Oils. JA)CS 66(7) 953–960.*

* cited by examiner

*Primary Examiner*—Carolyn Paden
(74) *Attorney, Agent, or Firm*—Bryan Cave LLP

(57) ABSTRACT

The present invention relates to stabilizing marine oil by treatment with silica in the presence or absence of carbon and vacuum steam deodorization at a temperature between about 140° C. and about 210° C. in the presence of 0.1–0.4% deodorized rosemary or sage extract If desired 0.01–0.03% ascorbyl palmitate and 0.05–0.2% mixed tocopherol can be added. A method of using such oil in food applications is provided. A method of identifying the sensory quality of unknown marine oils is also provided.

11 Claims, No Drawings

PREPARATION AND STABILIZATION OF FOOD-GRADE MARINE OILS

This is a continuation of U.S. application Ser. No. 09/608,401 filed Jun. 30, 2000, abn. which is a continuation of U.S. application Ser. No. 09/434,186 filed Nov. 4, 1999.

FIELD OF THE INVENTION

The present invention relates to processes for preparing and stabilizing food-grade marine oils.

BACKGROUND OF THE INVENTION

Marine oils have attracted substantial interest as a source of n-3 long-chain polyunsaturated fatty acids (LCPUFA), particularly eicosapentaenoic acid (EPA) and docosahexaenoic acid (DHA), which are of dietary significance. These LCPUFA contain 5 or 6 double bonds which render them prone to atmospheric oxidation accompanied by a fishy taste and smell. The increasing interest in LCPUFA has prompted research into methods of stabilizing fish oils against oxidation and off-flavor development Refined marine oils are initially free from a fishy taste and smell but reversion through oxidation occurs rapidly. Many attempts have been made to stabilize such oils by the addition of different anti-oxidants or mixtures thereof. However, all these attempts have failed so far, cf. R. J. Hamilton et al., Journal of American Oil and Chemist's Society (JAOCS), Vol. 75, no. 7, p. 813–822, (1998). Accordingly, there is a need for a process for stabilizing marine oils over a long period of time in a simple and economical way, where, even after a long period of storage, no fishy taste and smell occur.

Fully or partially refined marine oil which has been treated with silica and stabilized by incorporation in the thus-treated oil of a mixture of lecithin, ascorbyl palmitate, and alpha-tocopherol in accordance with the procedure described in EP 612 346 and its U.S. counterpart U.S. Pat. No. 5,855,944 (U.S. Pat. No. 5,855,944) reportedly displays excellent Rancimat stability and good application performance for health food supplements. In a particular embodiment of the procedure described in EP 612 346/U.S. Pat. No. 5,855,944, the filly or partially refined marine oil is treated with silica having a surface area greater than 500 $m^2/g$, and the silica-treated oil is then subjected to a soft vacuum steam deodorization at a temperature between about 140° C. and about 210° C.; then lecithin, ascorbyl palitate and a tocopherol in the ratio of 6–3: 4–2: 8–4 are incorporated in the thus-treated oil, whereby the resulting stabilization is reported to last for several months. In dairy applications, such as yogurt and milk drinks, however, the so-treated and stabilized oil develops a strong fishy smell and taste.

Refined marine oil which has been treated with an adsorbent such as silica and stabilized with 0.1% deodorized rosemary extract (HERBALOX "O", available from Kalsec, Inc. of Kalanmazoo, Mich.) and sage extract in a manner analogous to the procedure described in EP 340 635 reportedly has a hereby taste and smell which can be detected in food applications. This hereby taste and smell reportedly suppresses the taste and smell of fish. In dairy applications, the use of as little as 0.03% of HERBALOX "O" and sage extract in the marine oil results in a very strong hereby taste and smell which prevents the use of this oil in these applications.

SUMMARY OF THE INVENTION

Accordingly, the present invention provides a process for preparing and stabilizing food-grade marine oil which includes treating marine oil with silica optionally in the presence of carbon, vacuum steam deodorizing the marine oil at a temperature between about 140° C. and about 210° C. in the presence of 0.1–0.4% rosemary or sage extract, and, optionally, adding 0.01–0.03% ascorbyl palmitate and 0.05–0.2% mixed tocopherol to the marine oil after the deodorizing.

DETAILED DESCRIPTION OF THE INVENTION

It has now surprisingly been found in accordance with the present invention that marine oil which has been treated with silica in accordance with the procedure described in EP 612 346/U.S. Pat. No. 5,855,944 can be stabilized over a long period of time without the occurrence of fishy taste and smell by vacuum steam deodorization at a temperature between about 140° C. and about 210° C., in the presence of 0.1–0.4% of deodorized rosemary or sage extract. The treating of the oil with silica may be by combining (i.e., adding or mixing the oil with silica). The treatment of the oil with silica can suitably be carried out in one embodiment by contacting the oil with the silica in a silica-filled column or stirred reactor vessel or a combination thereof Batch, semi-batch or continuous operation is feasible. Silica having a surface area of more than 500 $m^2/g$ is suitably used. It is preferred to carry out this treatment at about room temperature, although lower or, especially, higher temperatures may also be used if desired. Further, it is preferred to perform this embodiment under the atmosphere of an inert gas, especially nitrogen. The contact time between the oil and the silica can be varied within wide limits and can be a few seconds to several days. In this connection, the flow rate at which the oil passes through the silica in a column procedure will depend on factors such as the type and particle size of the chosen silica, the dimensions of the column and the like.

In another embodiment, an oil/solvent miscella is passed through a silica column The solvent is preferably a food grade approved apolar solvent, preferably a hydrocarbon and especially hexane. This embodiment can be carried out, for example, by dissolving the oil in the solvent to provide a solution containing about 20–60%, preferably 33%, oil by weight, passing the solution through silica in a column or stirred reactor vessel or a combination thereof using a ratio of miscella to silica of 20:1 to 5:1, preferably 15:1, (wt./wt.), filtering and then removing the solvent by distillation. Here again, the contact time between oil and the silica can be varied within wide limits and can be a few seconds to several days.

The treatment with silica described hereinbefore can also be carried out in the presence of carbon. The carbon which is used is preferably dried or substantially freed from water 2a before or during the process and, furthermore, preferably has a surface area of more than 1100 $m^2/g$. Examples of suitable carbons are those available as NORIT, e.g. NORIT CA1, and similar activated carbons.

The fully refined marine oil used in the present invention is one which has been neutralized, bleached and deodorized in a conventional manner. The oil can be, for example, menhaden oil, herring oil, sardine oil anchovy oil, pilchard oil, tuna oil, shark oil, hake oil, etc., or a blend of two or more of these oils.

Factors associated with the fishy taste and smell of a marine oil are not well defined. In order to obtain more information as to which factors are responsible for the fishy taste and smell, 21 oil samples were analyzed in detail as shown and discussed below. Samples 1–10 used in these analytical proceedings are commercially available standard fish oils from suppliers throughout the world and are regarded as being "aged" because of the delays in refining them further in accordance with the procedure described in EP 612 346/U.S. Pat. No. 5,855,944, whereas samples 11–15 are refined fish oils where it is known that both the extraction and refining have been performed immediately after the fish have been caught or with minimum delay only. Samples 16–17 are oils of fungal origin Samples 18–21 have been produced from commercially available fish oils in accordance with the procedure described in EP 612 346/U.S. Pat. No. 5,855,944 in which, however, a special short path distillation step has been included at the start of the process to trap smell molecules for use as described below. The purpose to this wide trawl (diversified catch) is to have as representative a range as possible of refined oils containing EPA and DHA.

Table 1 records the influence of the acid value, the EPA and, respectively, DHA content, the color and the pro-oxidant iron and copper levels on sensory responses of a trained panel to the 21 oil samples described above.

The analysis for the determination of the EPA and DHA content and, respectively, the proxidant iron and copper levels were performed according to analytical methods known in the art. For determining the acid value, i.e., the number of milligrams of potassium hydroxide required to neutralize the free fatty acids in 1 gram of oil, the oil sample is titrated with 0.1N aqueous potassium hydroxide solution using a 1% phenolphthalein indicator. The size of the sample was determined as follows:

| Expected acid value | Test sample (g) |
|---|---|
| >0.5 | 40 |
| 0.5 to 1 | 20 |
| 1 to 5 | 5 |
| 5 to 10 | 2.5 |
| 10 to 20 | 1 |
| >20 | 0.5 |

The color is determined by means of a Lovibond tintometer Model E AF 900 by matching the color of light transmitted through a specified depth of oil to the color of the light originating from the same source, transmitted through standard color slides. The results are expressed in terms of the red (R), yellow (Y), and blue (B) units to obtain the match and the size of the cell used. Taste and smell are sensorically evaluated by a trained panel of 12–15 persons. The panelists are asked to rank the samples in terms of perception of fishy taste and smell. A hedonic scale of 1 to 5 is used to express the extent of fishiness in which 1 represents no fishy taste or smell while 5 represents a very strong fishy taste or smell. The samples are coded using a three-digit code and 10–15 ml of each sample are submitted to the panel in a plastic beaker at 22° C. The products are evaluated after processing after 4 weeks and, respectively, 12 weeks storage at a temperature of 22° C. in aluminum containers.

Table 2 shows the effect of prima and secondary oxidation levels on the taste and smell of the same marine oils as in Table 1. Primary oxidation is measured as the peroxide value of the oils in milliequivalent (meq)/kg of oil. Secondary oxidation is measured in two ways: The first is by the reaction of unsaturated aldehydes in the oil with anisidine. The second is by the reaction of a alkenals and alkadienals in the oil with NN-dimethyl-p-phenylenediamine.

For determining the peroxide value, the oil is treated in a solution of acetic acid and chloroform with a solution of iodide, and subsequently the free iodine is titrated with a solution of sodium thiosulphate. The size of the sample was determined as follows:

| Expected peroxide value | Test sample (g) |
|---|---|
| <1 | 10 |
| 1 to 5 | 2 |
| 5 to 10 | 1 |
| >10 | 0.5 |

The p-anisidine value as used herein is defined as 100 times the absorbence measured at 350 nm in a 1 cm cell of a solution containing 1.0 g of the oil in 100 ml of a mixture of hexane and a solution of p-anisidine in glacial acetic acid (0.025 g/100 ml of glacial acetic acid). The size of the sample was determined as follows:

| Expected p-anisidine value | Test sample (g) |
|---|---|
| 0–5 | 5 |
| 5–10 | 3 |
| 10–20 | 2 |
| 20–30 | 1 |

The aldehyde values were determined based on a method described by K. Miyashita et al., JAOCS, Vol. 68 (1991), which discloses a process in which N,N-diethyl-p-phenylenediamine is reacted with aldehydes in the presence of acetic acid. The three aldehyde classes (alkanal, alkenal, and alkadienal) are determined by visible absorption at 400, 460 and 500 nm, respectively. The aldehyde values are expressed in mmole/kg.

Furthermore, the level of smell molecules in each of these oils has been measured by static headspace coupled to GC/MS (gas chromatograph/mass spectrometer). The oil to be measured (samples of 1 g each) is crimp sealed into a headspace vial (22 ml) in a nitrogen atmosphere and heated at 120° C. for 15 minutes in a headspace autosampler. A measured of the headspace is automatically injected onto a GC/MS using a heated transfer line. chromatograph is used to separate the molecules, and the mass spectrometer is used to identify and quantify the separated molecules. The results obtained are shown in Table 3.

TABLE 1

| | Acid Value | EPA (%) | DHA (%) | Color | Copper (ppb) | Iron (ppb) | Taste | Smell |
|---|---|---|---|---|---|---|---|---|
| Standard Fish | | | | | | | | |
| 1 | 0.07 | 17.4 | 10.1 | 3.5R 23Y | 13 | 39 | 2.3 | 0.7 |
| 2 | 0.06 | 18.8 | 9.1 | 1.1R 20Y | 9 | 10 | 3.2 | 1.5 |
| 3 | 0.02 | 15.7 | 6.3 | 2.4R 24Y | 6 | 16 | 2.8 | 1.2 |
| 4 | 0.04 | 11.6 | 12.1 | 2.6R 31Y | 12 | 22 | 4.0 | 3.0 |
| 5 | 0.17 | 17.6 | 10.3 | 2.5R 20Y | 17 | 24 | 2.1 | 0.8 |
| 6 | 0.08 | 16.9 | 11.7 | 3.1R 30Y | 31 | 29 | 2.8 | 1.6 |
| 7 | 0.04 | 6.7 | 27.7 | 1.6R 20Y | 14 | 25 | 1.2 | 0.6 |
| 8 | 0.20 | 6.7 | 27.5 | 3.6R 32Y | 37 | 9 | 1.2 | 0.5 |
| 9 | 0.04 | 6.6 | 27.3 | 1.5R 23Y | 13 | 18 | 2.7 | 1.6 |
| 10 | 0.08 | 6.7 | 28.0 | 1.2R 31Y | 12 | 12 | 3.6 | 2.0 |
| Fresh Fish | | | | | | | | |
| 11 | 0.32 | 6.9 | 13.0 | 0.8R 15Y | 3 | 27 | 2.2 | 0.6 |
| 12 | 0.30 | 8.7 | 7.5 | 2.0R 25Y | 7 | 24 | 2.4 | 0.8 |
| 13 | 0.20 | 11.8 | 13.3 | 1.6R 20Y | 6 | 13 | 1.5 | 1.0 |
| 14 | 0.23 | 10.3 | 11.8 | 0.5R 5.4Y | 8 | 26 | 2.6 | 1.3 |
| 15 | 0.23 | 8.6 | 12.6 | 1.5R 15Y | 6 | 29 | 2.8 | 1.0 |
| Single Cell | | | | | | | | |
| 16 | 0.02 | 2.3 | 36.9 | 1.5R 32Y | 7 | 10 | 1.7 | 0.9 |
| 17 | 0.77 | 0.4 | 31.0 | 1.2R 14Y | 22 | 34 | 2.5 | 0.9 |
| Standard Fish Distilled | | | | | | | | |
| 18 | 0.2 | 18.0 | 10.5 | 2.2R 20Y | 3 | 24 | 0.7 | 0.7 |
| 19 | 0.23 | 18.0 | 10.4 | 2.2R 20Y | 5 | 24 | 0.6 | 0.7 |
| 20 | 0.22 | 18.1 | 10.5 | 2.2R 23Y | 8 | 30 | 0.6 | 0.6 |
| 21 | 0.19 | 17.9 | 10.4 | 2.3R 22Y | 7 | 24 | 1.0 | 0.5 |

Table 1 shows that there is no correlation between the acid value, the EPA and DHA content, the color and pro-oxidant iron and copper levels, and the taste and smell of these marine oils.

TABLE 2

| | Primary oxidation | Secondary oxidation | | | | | |
|---|---|---|---|---|---|---|---|
| | | p-Anisidine | Aldehydes | | | | |
| Description | Peroxide value | value | A | B | C | Taste | Smell |
| Standard Fish | | | | | | | |
| 1 | 0.4 | 19.8 | 2.41 | 0.3 | 0.9 | 2.3 | 0.7 |
| 2 | 0.5 | 12.62 | 1.46 | 0.15 | 0.54 | 3.2 | 1.5 |
| 3 | 0.8 | 8.7 | 0.54 | 0.08 | 0.34 | 2.8 | 1.2 |
| 4 | 0.7 | 15.31 | 1.87 | 0.29 | 0.68 | 4.0 | 3.0 |
| 5 | 0 | 3.77 | 0.6 | 0.09 | 0.17 | 2.1 | 0.8 |
| 6 | 0 | 4.24 | 1.02 | 0.11 | 0.23 | 2.8 | 1.6 |
| 7 | 0.4 | 8.24 | 1.94 | 0.24 | 0.66 | 1.2 | 0.8 |
| 8 | 0.4 | 6.81 | 1.09 | 0.15 | 0.35 | 1.2 | 0.5 |
| 9 | 0.5 | 6.81 | 1.06 | 0.14 | 0.32 | 2.7 | 1.6 |
| 10 | 2.1 | 9.42 | 0.97 | 0.18 | 0.36 | 3.6 | 2.0 |
| Fresh Fish | | | | | | | |
| 11 | 0 | 0.46 | 0.35 | 0.04 | 0.03 | 2.2 | 0.6 |
| 12 | 0 | 1.58 | 2.6 | 0.05 | 0.06 | 2.4 | 0.8 |
| 13 | 0 | 1.17 | 0.08 | 0.03 | 0.04 | 1.5 | 1.0 |
| 14 | 0 | 1.19 | 0.16 | 0.02 | 0.04 | 2.6 | 1.3 |
| 15 | 0 | 0.6 | 0.09 | 0.02 | 0.03 | 2.8 | 1.0 |
| Single Cell | | | | | | | |
| 16 | 4 | 6.58 | 1.13 | 0.26 | 0.3 | 1.7 | 0.9 |
| 17 | 0 | 1.45 | 0.45 | 0.03 | 0.04 | 2.5 | 0.9 |

TABLE 2-continued

| | Primary oxidation | Secondary oxidation | | | | | |
|---|---|---|---|---|---|---|---|
| | | p-Anisidine | Aldehydes | | | | |
| Description | Peroxide value | value | A | B | C | Taste | Smell |
| Standard Fish Distilled | | | | | | | |
| 18 | 0 | 6.12 | 0.9 | 0.14 | 0.27 | 0.7 | 0.7 |
| 19 | 0 | 4.96 | 0.85 | 0.12 | 0.25 | 0.6 | 0.7 |
| 20 | 0 | 4.84 | 0.83 | 0.12 | 0.25 | 0.6 | 0.6 |
| 21 | 0 | 5.04 | 0.76 | 0.12 | 0.24 | 1.0 | 0.5 |

A = alkanals, B = alkenals, C = alkadienals

Table 2 shows that the oxidation indicators are not capable of distinguishing oils with a good taste and smell from oils with a bad taste and smell.

TABLE 3

| Description | Propanal | Propenal | Butanal | Ethyl Furan | Pentanal | Penten-3-one | Hexanal | Penten-3-ol | Heptanal |
|---|---|---|---|---|---|---|---|---|---|
| Standard fish | | | | | | | | | |
| 1 | 104 | 550 | <40 | 11 | <460 | <90 | 590 | 218 | <100 |
| 2 | <90 | 371 | <40 | 12 | <460 | <90 | 578 | 154 | <100 |
| 3 | 214 | 840 | <40 | 28 | <460 | <90 | 425 | 407 | <100 |
| 4 | 516 | 1587 | 62 | 41 | <460 | 151 | <100 | 572 | <100 |
| 5 | 134 | 356 | <40 | <10 | <460 | 405 | <100 | 189 | <100 |
| 6 | <90 | 280 | <40 | <10 | <460 | <90 | <100 | <90 | <100 |
| 7 | 599 | 4059 | <40 | 91 | <460 | 425 | <100 | <90 | <100 |
| 8 | 967 | 934 | 61 | 79 | <460 | 175 | <100 | 359 | <100 |
| 9 | 566 | 3877 | 41 | 85 | <460 | 405 | <100 | 1501 | <100 |
| 10 | 668 | 3430 | 79 | 58 | <460 | 452 | <100 | 1610 | <100 |
| Fresh fish | | | | | | | | | |
| 11 | <90 | ND | <40 | <10 | <460 | <90 | <100 | <90 | <100 |
| 12 | 109 | ND | <40 | 15 | <460 | <90 | <100 | <90 | <100 |
| 13 | <90 | ND | <40 | <10 | <460 | <90 | <100 | <90 | <100 |
| 14 | <90 | ND | <40 | <10 | <460 | <90 | <100 | <90 | <100 |
| 15 | <90 | ND | <40 | <10 | <460 | <90 | <100 | <90 | <100 |
| Single cell | | | | | | | | | |
| 16 | 1992 | 1587 | 62 | 41 | <460 | 151 | <100 | 572 | <100 |
| 17 | 296 | ND | <40 | 35 | <460 | 293 | 231 | 261 | <100 |
| Standard fish distilled | | | | | | | | | |
| 18 | <90 | 122 | <40 | <10 | <460 | <90 | 902 | 91 | <100 |
| 19 | <90 | 190 | <40 | <10 | <460 | <90 | 1319 | 92 | <100 |
| 20 | <90 | 170 | <40 | <10 | <460 | <90 | 1328 | <90 | <100 |
| 21 | <90 | 203 | <40 | <10 | <460 | <90 | 1303 | 91 | <100 |

| Description | Hexenal | Octanal | Heptenal | Nonanal | Hexadienal | Octenal | Heptadienal | Taste | Smell |
|---|---|---|---|---|---|---|---|---|---|
| Standard fish | | | | | | | | | |
| 1 | <470 | <470 | <490 | <910 | <960 | <940 | 791 | 2.3 | 0.7 |
| 2 | <470 | <470 | <490 | <910 | <960 | <940 | 757 | 3.2 | 1.5 |
| 3 | <470 | <470 | <490 | <910 | <960 | <940 | 701 | 2.8 | 1.2 |
| 4 | <470 | <470 | <490 | <910 | <960 | <940 | <500 | 4.0 | 3.0 |
| 5 | <470 | <470 | <490 | <910 | <960 | <940 | <500 | 2.1 | 0.8 |
| 6 | <470 | <470 | <490 | <910 | <960 | <940 | <500 | 2.8 | 1.6 |
| 7 | <470 | <470 | 1340.0 | <910 | 1400 | <940 | <500 | 1.2 | 0.8 |
| 8 | <470 | <470 | <490 | <910 | <960 | <940 | <500 | 1.2 | 0.5 |
| 9 | <470 | <470 | <490 | <910 | <960 | <940 | <500 | 2.7 | 1.6 |
| 10 | <470 | <470 | <490 | <910 | <960 | <940 | 1649 | 3.6 | 2.0 |
| Fresh fish | | | | | | | | | |
| 11 | <470 | <470 | <490 | <910 | <960 | <940 | <500 | 2.2 | 0.6 |
| 12 | <470 | <470 | <490 | <910 | <960 | <940 | <500 | 2.4 | 0.8 |
| 13 | <470 | <470 | <490 | <910 | <960 | <940 | <500 | 1.5 | 1.0 |
| 14 | <470 | <470 | <490 | <910 | <960 | <940 | <500 | 2.6 | 1.3 |
| 15 | <470 | <470 | <490 | <910 | <960 | <940 | <500 | 2.8 | 1.0 |

TABLE 3-continued

| Single cell | | | | | | | | | |
|---|---|---|---|---|---|---|---|---|---|
| 16 | <470 | <470 | <490 | <910 | <960 | <940 | <500 | 1.7 | 0.9 |
| 17 | <470 | <470 | <490 | <910 | <960 | <940 | <500 | 2.5 | 0.9 |
| Standard fish distilled | | | | | | | | | |
| 18 | <470 | <470 | <490 | <910 | <960 | <940 | <500 | 0.7 | 0.7 |
| 19 | <470 | <470 | <490 | <910 | <960 | <940 | 764 | 0.6 | 0.7 |
| 20 | <470 | <470 | <490 | <910 | <960 | <940 | 764 | 0.6 | 0.6 |
| 21 | <470 | <470 | <490 | <910 | <960 | <940 | 833 | 1.0 | 0.5 |

Table 3 shows that static headspace cannot distinguish between good and bad tasting marine oils.

Tables 1–3 also show that marine oils which have been refined soon after the oil has been extracted from freshly caught fish do not exhibit better sensory response than oils which have been refined from aged crude fish oil. However, levels of secondary anisidine reactives and aldehydes are extremely low in these fresh oils. These results suggest that whatever is responsible in the marine oil for the fishy taste and smell is present at extremely low levels which are below the detection limits of static headspace GC/MS. The data also show that neither anisidine nor aldehyde measurements are very useful in predicting the sensory quality of the oil because they are too insensitive.

Tables 1–3 show sensory data for single cell oils which demonstrate that they too may become fishy in both taste and smell. Table 1 also shows that, when using specially refined oils, it is possible to produce marine oils with excellent taste and smell, but with quality parameters such as anisidine, peroxide, iron, copper, color and static headspace values which are not different from those of oils having poor taste and smell.

To understand the extent to which fishy taste and smell occur in marine oils, efforts have been made to identify and quantify the molecules responsible for the fishy taste and smell. Marine oils (1 kg each) rich in EPA and/or DHA which had a strong fishy smell were passed slowly through a short path distillation apparatus at 120° C. and under reduced pressure (0.005 mbar). Two vacuum traps were connected in series, each cooled with liquid nitrogen, to collect the fishy volatiles which were removed by this process. These oils were then deodorized at 190° C. and are designated in Tables 1–3 as samples 18–21. Even though their traditional quality parameters are no different from those of oils which are deemed to be fishy, they had little or no fishy taste The condensation products captured in the vacuum traps were dissolved in methyl tert butyl ether and subjected to the olfactory detector GC/MS to identify fishy molecules which had been removed by this process. In the olfactory detector GC/MS, the outlet stream from a gas chromatograph is split and routed to two different detectors. In the present case, the detectors used were the mass spectrometer and the human nose. Such a system allows peaks to be identified by the MS and assigned smell by an operator.

A number of very potent smell molecules were identified in the distillation products and are set forth in Table 4.

TABLE 4

| Target Molecule | Characteristic According To Prior Art |
|---|---|
| 4-heptenal | Fish oil |
| 1-octen-3-one | Mushroom |
| 1,5(Z)-octadien-3-ol | Mushroom |
| 1,5(Z)-octadien-3-one | Metallic/fresh fish |
| (E,E)-2,4-heptadienal | Oxidized oil |
| (E)-2-octenal | Oxidized oil |
| (Z)-6-nonenal | Oxidized oil/putty/linseed oil |
| (E,Z)-2,6-nonadienal | Cucumber/fresh fish |
| (E)-2-nonenal | Oxidized oil |
| (E,Z)-1,3,5-undecatriene | Cod liver oil |
| (E,E)-2,4-decadienal | Fish/oxidized oil |

As can be seen from Table 3, only a few of the molecules listed in Table 4 could be identified by static headspace. Thus, a more sensitive method was required to remove headspace molecules from the oils. The detection limits for 2-octenal and 2,4-hexadienal, for example, were 940 ppb and 500 ppb, respectively. In order to improve the sensitivity of detection, the technique of dynamic headspace has been used. According to this technique, 2 g aliquots of oil were heated to 75° C. in a water bath purged with helium (150 ml/min) through a Tekmar purge glass apparatus onto Perkin Elmer cartridges containing TENAX adsorbent (Enka Research Institute, Amheim). The dynamic headspace was measured by is GC/MS using a 30 m column of DB5-MS (1 μm film thickness).

Table 5 below shows the taste panel response to a number of matures of marine oils and the dynamic headspace profile of a number of molecules. They have been identified by GC/MS and olfactory detector GC/MS. As can be seen, some of these molecules may be detected to single figure ppb levels, using dynamic headspace. The importance of the data in Table 5 is that they explain why the data in Tables 1–3 cannot possibly correlate with marine oil taste and smell, and they also demonstrate the very small amount of oxidation which is required before the oil deteriorates to an unacceptable quality in respect of taste and smell.

TABLE 5

| | | | Concentration (ppb) | | | | | | |
|---|---|---|---|---|---|---|---|---|---|
| Sample No. | oil type | Taste | 2,6-nonadienal | 1,5-octdien-3-one | 4-heptenal | 2-hexenal | 3,6-nonadienal | 2,4-heptadienal | Taste factor |
| 1 | EPA | strong fish | 53 | 69 | 26 | 146 | 457 | 213 | 4 |
| 2 | EPA | middle fish | 37 | 27 | 33 | 100 | 288 | 168 | 3 |

TABLE 5-continued

| | | | Concentration (ppb) | | | | | | |
|---|---|---|---|---|---|---|---|---|---|
| Sample No. | oil type | Taste | 2,6-nonadienal | 1,5-octdien-3-one | 4-heptenal | 2-hexenal | 3,6-nonadienal | 2,4-heptadienal | Taste factor |
| 3 | EPA | strong fish | 68 | 54 | 53 | 232 | 710 | 542 | 4 |
| 4 | EPA | no fish | 28 | 151 | 35 | 113 | 254 | 282 | 1 |
| 5 | EPA | no fish | 19 | 74 | 31 | 79 | 223 | 208 | 1 |
| 6 | EPA | middle fish | 40 | 101 | 102 | 309 | 240 | 417 | 3 |
| 7 | EPA | no fish | 21 | 36 | 15 | 50 | 72 | 81 | 1 |
| 8 | DHA | middle fish | 27 | 79 | 61 | 230 | 324 | 257 | 3 |
| 9 | DHA | no fish | 23 | 64 | 15 | 57 | 101 | 128 | 1 |
| 10 | EPA | no fish | 16 | 42 | 10 | 0 | 70 | 92 | 1 |
| 11 | DHA | slight fish | 34 | 123 | 56 | 313 | 182 | 277 | 2 |
| 12 | EPA | no fish | 18 | 96 | 13 | 36 | 128 | 168 | 1 |
| 13 | DHA | no fish | 16 | 52 | 9 | 40 | 104 | 107 | 1 |
| 14 | DHA | no fish | 17 | 41 | 16 | 40 | 61 | 75 | 1 |
| 15 | DHA | slight fish | 25 | 69 | 26 | 104 | 156 | 198 | 2 |
| 16 | EPA | middle fish | 25 | 64 | 23 | 89 | 321 | 212 | 3 |
| 17 | EPA | no fish | 20 | 54 | 13 | 54 | 70 | 111 | 1 |
| 18 | EPA | middle fish | 28 | 113 | 41 | 147 | 441 | 334 | 3 |
| 19 | EPA | no fish | 21 | 45 | 7 | 39 | 96 | 182 | 1 |
| 20 | EPA | slight fish | 22 | 109 | 13 | 64 | 305 | 240 | 2 |
| 21 | EPA | no fish | 13 | 80 | 8 | 38 | 194 | 158 | 1 |
| 22 | DHA | middle fish | 22 | 157 | 31 | 101 | 719 | 563 | 3 |
| 23 | DHA | no fish | 15 | 78 | 6 | 48 | 216 | 215 | 1 |
| 24 | EPA | no fish | 14 | 55 | 7 | 38 | 109 | 116 | 1 |
| 25 | DHA | no fish | 0 | 52 | 8 | 25 | 78 | 70 | 1 |
| 26 | DHA | slight fish | 39 | 111 | 12 | 41 | 239 | 201 | 2 |
| 27 | DHA | no fish | 0 | 0 | 4 | 9 | 63 | 56 | 1 |
| 28 | DHA | no fish | 18 | 69 | 11 | 38 | 159 | 153 | 1 |
| 29 | EPA | very strong fish | 646 | 587 | 1135 | 4105 | 5015 | 3690 | 5 |
| 30 | DHA | no fish | 0 | 0 | 13 | 40 | 105 | 111 | 1 |
| 31 | DHA | slight fish | 20 | 0 | 9 | 33 | 84 | 61 | 2 |
| 32 | DHA | no fish | 0 | 71 | 7 | 32 | 164 | 129 | 1 |
| 33 | DHA | no fish | 0 | 69 | 11 | 39 | 119 | 91 | 1 |
| 34 | DHA | no fish | 0 | 76 | 7 | 51 | 177 | 123 | 1 |
| 35 | DHA | no fish | 0 | 98 | 2 | 42 | 137 | 105 | 1 |
| 36 | DHA | no fish | 13 | 34 | 6 | 32 | 44 | 34 | 1 |

Table 6 below shows the excellent agreement between the level of 6 specially selected molecules in the headspace of the oils and the ranking by the taste panel using a multiple discriminant analysis (MDA). MDA is a statistical test for determining whether a given classification of cases into groups is a likely one. It will indicate whether the group assignment of a case is true or false. The final data are presented in a table with rows and columns corresponding to actual and estimated group membership, respectively. In the ambit of the present invention, the classification obtained from the sensorical evaluation by the taste panel was the taste factor. The MDA analysis was done through a statistical package called UNISTAT version 4.51.

TABLE 6

| | Group 1 | Group 2 | Group 3 | Group 4 | Group 5 |
|---|---|---|---|---|---|
| Group 1 | 22 | 0 | 0 | 0 | 0 |
| | 100% | 0% | 0% | 0% | 0% |
| Group 2 | 0 | 5 | 0 | 0 | 0 |
| | 0% | 100% | 0% | 0% | 0% |
| Group 3 | 0 | 0 | 6 | 0 | 0 |
| | 0% | 0% | 100% | 0% | 0% |
| Group 4 | 0 | 0 | 0 | 2 | 0 |
| | 0% | 0% | 0% | 100% | 0% |
| Group 5 | 0 | 0 | 0 | 0 | 1 |
| | 0% | 0% | 0% | 0% | 100% |

TABLE 6-continued

| | Group 1 | Group 2 | Group 3 | Group 4 | Group 5 |
|---|---|---|---|---|---|
| Group 1 | Not fishy | | | | |
| 2 | Slight fishy | | | | |
| 3 | Middle fishy | | | | |
| 4 | Strong fishy | | | | |
| 5 | V strong fishy | | | | |
| Molecule | Retention Index | Comparison to standard retention time | Mass spectrum | | |
| (E)-2-hexenal | 861 | Yes | Yes | | |
| (Z)-4-heptenal | 903 | Yes | Yes | | |
| 1,5-(Z)-octadien-3-one | 986 | Yes | Yes | | |
| (E,E)-2,4 heptadienal | 1004 | Yes | Yes | | |
| 3,6-nonadienal | 1109 | No | Yes | | |
| (E,Z)-2,6-nonadienal | 1159 | Yes | Yes | | |

The retention index of a compound is calculated from injections of C5–C15 saturated straight chain hydrocarbons under the same chromatographic conditions as the analysis of interest, and is similar to its retention time in that the longer it is retained on a GC column, the greater is its retention index/time. The use of the retention indices rather than retention times makes the information more rigorous and transferable, although the retention indices are still dependant on the column phase and chromatographic conditions, but still minimize instrument dependent variables.

In order for a peak on a GC trace to be accepted as having a certain identity, certain conditions must be met. The traditional condition with GC is that it should have the same retention index/time as an authentic standard. Of the 6 molecules listed, standards were obtained for 5 of them. Alternatively, mass spectra may be used as an additional tool to confirm peak identity.

rosemary extract as a stabilizer of marine oil after deodorization, is, even at the low amount of 0.2%, disadvantageous due to the powerful hereby smell of the commercial deodorized rosemary extract, particularly if it is put into dairy food applications. This makes it impossible to use the dose benefits shown in Table 7.

It has also been found in accordance with the present invention that adding the rosemary extract to the oil before deodorization removes the powerful smell without removing or destroying the anti-oxidant activity. The results of the relevant experiments are set forth in Tables 8 and 9.

Table 8 below shows a range of headspace molecules which describe the headspace of deodorized rosemary extracts at a concentration of 0.2% added to deodorized marine oil after deodorization and, respectively, 0.2% and 0.4% added before deodorization. In the latter case, two deodorization temperatures are given.

TABLE 8

| HERBALOX "O" Addition | 0.2% After Deodorization | 0.4% Before Deodorization | 0.4% Before Deodorization | 0.2% Before Deodorization | 0.2% Before Deodorization |
|---|---|---|---|---|---|
| Temperature | — | 150° C. | 190° C. | 150° C. | 190° C. |
| | % Normalized/Relative | % Removed | % Removed | % Removed | % Removed |
| Limonene | 100/4.7 | 17 | 20 | 50 | 50 |
| Eucalyptol | 100/3.5 | 100 | 100 | 100 | 100 |
| Linalool | 100/1.5 | 100 | 100 | 100 | 100 |
| Linalyl propanoate | 100/3.8 | 100 | 100 | 100 | 100 |
| Camphor | 100/20.3 | 97 | 99 | 100 | 100 |
| Iso-Borneol | 100/3.8 | 100 | 100 | 93 | 90 |
| Fenchyl acetate | 100/27.3 | 100 | 100 | 100 | 100 |
| Vebenone | 100/3.0 | 100 | 100 | 100 | 100 |
| Bornyl acetate | 100/1.2 | 100 | 100 | 100 | 100 |
| Copaene (1) | 100/1.8 | 100 | 100 | 100 | 100 |
| Ioscaryophyllene | 100/0.6 | 20 | 20 | 20 | 20 |
| Caryophyllene | 100/27.9 | 84.8 | 100 | 100 | 100 |
| Copaene | 100/0.5 | 100 | 100 | 100 | 100 |

Table 7 below shows the effect of increasing concentration of deodorized rosemary extract on the rancimat stability of a marine oil by adding it after deodorization.

TABLE 7

| Deodorized HERBALOX "O" added (%) | Rancimat Induction Time (100° C.) (hours) |
|---|---|
| 0 | 1.70 |
| 0.25 | 3.02 |
| 0.5 | 3.87 |
| 0.75 | 4.93 |
| 1.0 | 5.45 |
| 1.5 | 5.73 |
| 2.0 | 6.98 |
| 2.5 | 7.65 |
| 3.0 | 8.23 |
| 3.5 | 9.28 |
| 4.0 | 10.7 |

Table 7 shows that between 0 and 4% addition of rosemary extract, the rancimat induction time and, thus, the rancimat stability of marine oil, increases with an increasing amount of rosemary extract. Nevertheless, the use of The relative values set forth in column 2 of Table 8 were derived from the analysis of marine oil with 0.2% HERBALOX "O" added after deodorizing. When the oils are deodorized it is necessary to have a concentration against which it is possible to measure removal of the headspace molecules. Therefore, the concentration of each compound found in the experiment in which the rosemary extract was added after removal was taken as 100%, and the effects of deodorizing were measured against this level.

Table 8 also shows that when a mineral oil to which 0.2% of rosemary oil has been added before deodorization, is deodorized at 150° C. or 190° C., virtually all of these spicy molecules are removed from the oil. With 0.4% addition, removal of most of the spicy is molecules is low; two of the main components, i.e. camphor and caryophyllene, are not completely removed.

The hereby smell in an oil deodorized at 150° C. with 0.4% addition of rosemary extract before deodorization is still strong, whereas an oil with only 0.2% rosemary extract added does not have any hereby smell.

Table 9 below shows the effect on the anti-oxidant system of the following variables: the deodorization temperature, the anti-oxidant mixture, and the additional of rosemary before or after the deodorization.

TABLE 9

| Addition | HERBALOX "O" (%) | Sage Extract (%) | Ascorbyl Palmitate (%) | Mixed Tocopherol (%) | Deodorization Temperature (° C.) | Rancimat Induction Time (hours) |
|---|---|---|---|---|---|---|
| — | — | — | — | — | — | 1.7 |
| After | 0.2 | — | — | — | — | 3.0 |
| After | 0.2 | — | — | — | 150 | 3.0 |
| After | 0.2 | — | — | — | 190 | 2.9 |
| Before | 0.2 | — | — | — | 150 | 3.3 |
| Before | 0.2 | — | — | — | 190 | 4.1 |
| Before | 0.2 | — | 0.02 | 0.1 | 150 | 5.4 |
| Before | 0.2 | — | 0.02 | 0.1 | 190 | 6.2 |
| After | — | 0.2 | — | — | 190 | 2.3 |
| Before | — | 0.2 | — | — | 190 | 3.4 |
| Before | — | 0.2 | 0.02 | 0.1 | 190 | 5.3 |

As shown in Table 9, adding 0.2% rosemary extract to the marine oil without deodorizing increases the rancimat stability from 1.7 to 3.0.hours at 100° C. The same or approximately the same rancimat stability is seen when the rosemary extract is added to the oil after deodorizing at 150° C. and 190° C. A slight increase in rancimat stability is observed when sage extract is added to the oil after deodorizing at 190° C. If the rosemary extract is added to the oil before the deodorization at 150° C., there is a slightly increased rancimat stability, but by deodorizing at 190° C. in the presence of rosemary and sage extract, the rancimat stability of the oil is increased substantially to 4.1 and 3.4 hours, respectively. The addition of 0.02% ascorbyl palmitate and 0.1% mixed tocopherol after deodorization further enhances the rancimat stability of the oil. Thus, by deodorizing the oil at 190° C. and adding 0.2% rosemary and sage extract, respectively, before the deodorization, followed by 0.02 % ascorbyl palmitate and 0.1% mixed tocopherol after the deodorization, it is possible to increase the rancimat stability of the oil from 1.7 to 6.2 and 5.3 hours, respectively.

The present invention is a process for the preparation and stabilization of food-grade marine oil by treating marine oil with silica in the presence or absence of carbon, vacuum steam deodorizing at a temperature between about 140° C. and about 210° C. in the presence of 0.1–0.4% rosemary or sage extract and, if desired, adding 0.01–0.03% ascorbyl palmitate and 0.05–0.2% mixed tocopherol. The invention further includes methods of using the oil thus obtained in food applications. A further object of the present invention is a method of determining the sensory quality of an unknown marine oil by measuring the dynamic headspace profile of the marine oil with regard to the 6 following compounds: (2)oheptenal (E)-2-hexenal, 1,5-(Z)-octadien-3-one, (E,E)-2,4-heptadienal, 3,6-nonadienal, and (E,Z)2,6-nonadienal; and evaluating the results obtained against the results of the oils set forth in Table 5 by multiple discriminant analysis.

In the present invention, the silica treatment is preferably performed in the presence of carbon. The preferred temperature for the deodorization step, which may be carried out in conventional equipment, is between about 150° C. and about 190° C., for example, about 190° C. The preferred amount of deodorized rosemary or sage extract present during deodorization is about 0.2%. Furthermore, it is preferred to add after deodorization about 0.01–0.03%, preferably about 0.02%, of ascorbyl palmitate and about 0.05–0.2%, preferably about 0.1%, of mixed tocopherol. Any tocopherol can be used in this preferred embodiment, such as α and γ-tocopherols or a mixture of natural tocopherols.

The silica used in the present invention has been described in detail in EP 612 3461 / U.S. Pat. No. 5,855,944. This silica can be any conventional silica such as, for example, those available as TRISYL and TRISYL 300 (Grace), BRESORB (Akzo) or SD959, SD1027 and SORB-SIL C60 (Crosfield). It is preferred to use a silica which is dried or substantially freed from water before or during the process, i.e. which preferably has a water content of up to about 2%, preferably up to about 1%. The drying of the silica can be achieved, for example, by heating at about 100° C. for about 3 hours. Alternatively, the silica can be dried in heated oil under a vacuum or by azeotropic distillation. The carbon which can optionally be used has also been described in detail in EP 612 346/U.S. Pat. No. 5,855,944 and also above. All oils used in the examples were mixed with 5% silica and 2% activated carbon at 80° C. and then filtered as described in EP 612 346/U.S. Pat. No. 5,855,944.

The following examples are provided to further illustrate the process and methods of the present invention. These examples are illustrative only and are not intended to limit the scope of the invention in any way. The filtered product is referred to herein as "adsorbed oil" in the examples:

EXAMPLES

Example 1

950 g of adsorbed marine oil containing 11.0% EPA and 17.8% DHA were deodorized at 190° C. for 2 hours and then cooled to 600° C. The steam was stopped and replaced by a nitrogen purge for 5 minutes. The oil was then divided into aliquots and HBALOX "O" of up to 4% and was added to provide the rancimat stabilities as set forth in Table 7. To a separate aliquot of this oil, 0.2% HERBALOX "O" was added. The results of this study are recorded in Table 9. Samples of this oil were also dynamically purged to measure the content of spicy headspace molecules from the HERBALOX "O" addition. These results are recorded in Table 8.

Example 2

950 g of adsorbed marine oil containing 11.0% EPA and 17.8% DHA were deodorized at 150° C. for 2 hours and then cooled to 60° C. The steam was stopped and replaced by a nitrogen purge for 5 minutes. 0.2% HERBALOX "O" was added to this oil. The results of this study are recorded in Table 9. Samples of this oil were also dynarmcally purged to measure the content of spicy headspace molecules from the HERBALOX "O" addition. These results are recorded in Table 8.

Example 3

950 g of adsorbed marine oil containing 11.0% EPA and 17.8% DHA were mixed with 0.2% HERBALOX "O", deodorized at 190° C. for 2 hours, and then cooled to 60° C. The steam was stopped and replaced by a nitrogen purge for 5 minutes. The oil was then divided into two aliquots. One aliquot received no addition of further anti-oxidant. To the other aliquot 0.02% ascorbyl palmitate and 0.1% mixed tocopherol were added. The Rancimat stabilities were determined and are recorded in Table 9. Samples of this oil were also dynamically purged to measure the content of spicy headspace molecules from the HERBALOX "O" addition. The results are recorded in Table 8.

Example 4

950 g of adsorbed marine oil containing 11.0% EPA and 17.8% DHA were mixed with 0.2% HBERBALOX "O", deodorized at 150° C. for 2 hours, and then cooled to 600° C. The steam was stopped and replaced by a nitrogen purge for 5 minutes. The oil was then divided into two aliquots. To one aliquot, no anti-oxidant was added further. To the other aliquot, 0.02% ascorbyl palitate and 0.1% mixed tocopherol were added. The Rancimat stabilities IS were determined and are recorded in Table 9. Samples of this oil were also dynamically purged to measure the content of spicy headspace molecules from the HERB ALOX "O" addition The results are recorded in Table 8.

Example 5

950 g of adsorbed marine oil containing 11.0% EPA and 17.8% DHA were mixed with 0.4% HERBALOX "O", deodorized at 1500° C. for 2 hours, and then cooled to 60° C. The steam was stopped and replaced by a nitrogen purge for 5 minutes. The oil was then divided into aliquots which were dynamically purged to measure the content of spicy headspace molecules from the HERBALOX "O" addition. The results are recorded in Table 8.

Example 6

950 g of adsorbed marine oil contain 11.0% EPA and 17.8% DHA were mixed with 0.4% HERBALOX "O", deodorized at 190° C. for 2 hours, and then cooled to 60° C. The steam was stopped and replaced by a nitrogen purge for 5 minutes. The oil was then divided into aliquots which were dynamically purged to measure the content of spicy headspace molecules from the HERBALOX "O" addition. The results are recorded in Table 8.

Example 7

950 g of adsorbed marine oil containing 11.0% EPA and 17.8% DHA were deodorized at 190° C. for 2 hours, and then cooled to 60° C. The steam was stopped and replaced by a nitrogen purge for 5 minutes. 0.2% sage extract was added to this oil. The results of this study are recorded in Table 9.

Example 8

950 g of adsorbed marine oil containing 11.0% EPA and 17.8% DHA were mixed with 0.2% sage extract deodorized at 190° C. for 2 hours, and then cooled to 60° C. The steam was stopped and replaced by a nitrogen purge for 5 minutes. The oil was then divided into two aliquots. To one aliquot, no further antioxidant was added. To the other aliquot, 0.02% ascorbyl palmitate and 0.1% mixed tocopherol were added. The Rancimat stabilities were determined and are recorded in Table 9.

The following examples illustrate the use of marine oil obtained in accordance with the present invention in practical food applications. The oil used is hake oil containing 11.0% EPA and 17.8% DHA; it was deodorized at 190° C. in the presence of 0.2% HERBALOX "O", and will be named in the examples as "ROPUFA '30' n-3 Food Oil".

Example 9

Soft Drink With 30% Juice

| Typical serving: 300 ml<br>n-3 LCPUFA content: 75 mg/serving | |
|---|---|
| | [g] |
| Part I | |
| Orange concentrate 60.3° Brix, 5.15% acidity | 657.99 |
| Lemon concentrate 43.5° Brix, 32.7% acidity | 95.96 |
| Orange flavor, water soluble | 13.43 |
| Apricot flavor, water soluble | 6.71 |
| Water | 26.46 |
| Part II | |
| β-Carotene 10% CWS | 0.89 |
| Water | 67.65 |
| Part III | |
| Ascorbic acid | 4.11 |
| Citric acid anhydrous | 0.69 |
| Water | 43.18 |
| Part IV | |
| Stabilizer | 1.37 |
| Sodium benzoate | 2.74 |
| Water | 64.43 |
| Part V | |
| Orange flavor, oil soluble | 0.34 |
| Orange oil distilled | 0.34 |
| ROPUFA '30' n-3 Food Oil | 13.71 |
| Bottling syrup | |
| Soft drink compound | 74.50 |
| Water | 50.00 |
| Sugar syrup 60° Brix | 150.00 |

The bottling syrup was diluted with water to 11 ready to drink beverage.

Part I: All ingredients were mixed together without incorporation of air.

Part II: β-Carotene was dissolved in water.

Part III: Ascorbic acid and citric acid were dissolved in water.

Part IV: Sodium benzoate was dissolved in water. The stabilizer was added under stirring and swollen for 1 hour.

Part V: All ingredients were mixed together.

Parts I–V were mixed together before homogenization using first a Turrax and then a high pressure homogenizer ($p_1$=200 bar, $p_2$=50 bar).

Instead of using sodium benzoate, the beverage may be pasteurized. The beverage may also be carbonized.

Example 10

5 Cereal Bread

Typical serving: 100 g
n-3 LCPUFA content: 90 mg/serving

|  | [% wt] |
|---|---|
| 5 cereal flour | 100.00 |
| Water | 70.00 |
| Yeast | 4.00 |
| Salt | 2.00 |
| ROPUFA '30' n-3 Food Oil | 0.56 |

The yeast was dissolved in a part of the water. All ingredients including ROPUFA '30' n-3 Food Oil were mixed together to form a dough. Salt was added at the end of the kneading time. After fermentation, the dough was reworked and divided before a loaf was formed Before baking, the surface of the loaf was brushed with water and sprinkled with flour.

Parameters:

Kneading:

| Spiral kneading system | 4 min., 1$^{st}$ gear |
|---|---|
|  | 5 min., 2$^{nd}$ gear |
| Dough proofing: | 60 min |
| Dough temperature: | 22–24° C. |
| Proofing time: | 30 min. |

Baking

| Oven: | Dutch type oven |
|---|---|
| Baking temperature: | 250/220° C. |
| Baking time: | 50–60 min |
| Estimated baking loss: 10%. | |

Example 11

Table Margarine

60% fat
Typical serving: 30 g
n-3 LCPUFA content: 225 mg/serving

|  | [% wt] |
|---|---|
| Fat phase: | |
| Sunflower oil | 25.220 |
| Mixture of hardened rapeseed, soy, coconut and palm fat | 31.175 |
| ROPUFA '30' n-3 Food Oil | 3.000 |
| Emulsifier | 0.600 |
| Beta-Carotene 30% FS | 0.004 |
| Butter flavor, oil soluble. | 0.001 |
| Water phase: | |
| Water | 39.858 |
| Salt | 0.100 |
| Citric Acid | 0.042 |

Fat phase:
The fats were melted, but the temperature did not exceed 60° C. The oil was added and kept at the same temperature. Shortly before processing, the ROPUFA '30' n-3 Food Oil was added. Then all other oil soluble ingredients were added to the fat/oil mixed.

Water phase:
All water soluble ingredients were dissolved in water and pasteurized.

The water phase was added slowly to the oil phase (50° C.) and mixed with a high shear mixer to form a homogeneous emulsion The emulsion was crystallized in a margarine plant, equipped with a mutator, pinworker, and resting tube. The margarine was filled into cups at 200° C. and kept cool.

Example 12

Table Margarine

80% fat
Typical serving: 30 g
n-3 LCPUFA content: 225 mg/serving

|  | [% wt] |
|---|---|
| Fat phase: | |
| Sunflower oil | 30.850 |
| Mixture of hardened rapeseed, soy, coconut and palm fat | 45.800 |
| ROPUFA '30' n-3 Food Oil | 3.000 |
| Emulsifier | 0.250 |
| Beta-Carotene 30% FS | 0.008 |
| Butter flavor, oil soluble. | 0.090 |
| Water phase: | |
| Water | 19.910 |
| Salt | 0.100 |
| Citric Acid | 0.005 |
| Butter flavor, water soluble. | 0.005 |

Fat phase:
The fats were melted, but the temperature did not exceed 60° C. The oil was added to the fat mixture and kept at the same temperature. Shortly before processing, the ROPUFA '30' n-3 Food Oil was added. Then all other oil soluble ingredients were added to the fat-oil mixture.

Water phase:
All water soluble ingredients were dissolved in water and pasteurized.

The water phase was added slowly to the oil phase (50° C.) and mixed with a high shear mixer to form a homogeneous emulsion. The emulsion was crystallized in a margarine plant, equipped with a mutator, pinworker, and resting tube. The margarine was filled into cups at 15° C. and kept cool.

Example 13

Cookies

Type Mailänder
Typical serving: 25 g
n-3 LCPUFA content: 62.5 mg/serving

|  | [g] |
|---|---|
| Wheat Flour, type 550 | 410.0. |
| Sugar | 205.0 |
| Fat/Butter | 195.9 |
| ROPUFA '30' n-3 Food Oil | 9.1 |
| Whole egg (liquid) | 180.0 |
| Lemon Flavor | q.s. |
| Baking agent | q.s. |

The ROPUFA '30' n-3 Food Oil was added to the melted fat. All other ingredients were added slowly under mixing to form a sweet short pastry.

Afterwards, the pastry was maintained at 4° C. for at least 2 hours before flattening the pastry to a thickness of about 5 mm Pieces were cut out and brushed with egg yolk on the surface before baking:

| Baking: | |
|---|---|
| Oven: | fan oven |
| Baking temperature: | 180° C. |
| Baking time: | 15 min. |

Example 14

Toast

| Typical serving: 100 g<br>n-3 LCPUFA content: 90 mg/serving | |
|---|---|
|  | [% wt] |
| Wheat Flour, type 550 | 100.00 |
| Water | 60.00 |
| Yeast | 5.00 |
| Salt | 2.00 |
| Fat/Butter | 9.43 |
| ROPUFA '30' n-3 Food Oil | 0.57 |
| Malt | 1.00 |
| Emulsifier baking agent | 2.50 |

The yeast was dissolved in a part of the water. All ingredients were mixed together to form a dough including ROPUFA '30' n-3 Food Oil. Salt was added at the end of the kneading time. Afterwards the dough was reworked, divided, and placed in a baking tin for fermentation. After baking, the loaf was unmolded directly.

| Parameters: | |
|---|---|
| Kneading: | |
| Spiral kneading system | 5–6 min, 1st gear<br>3–4 min, 2nd gear |
| Dough proofing: | none |
| Dough temperature: | 22–24° C. |
| Proofing time: | 40 min |
| Baking: | |
| Oven: | Dutch type oven |
| Baking temperature: | 220° C. |
| Baking time: | 35–40 min. |

Example 15

Whole Flour Biscuits

| Typical serving: 25 g<br>n-3 LCPUFA content: 125 mg/serving | |
|---|---|
|  | [g] |
| Whole wheat flour | 355.0 |
| Fat | 195.3 |
| ROPUFA '30' n-3 Food Oil | 18.2 |
| Cane sugar | 177.5 |
| Almond, ground | 118.0 |

| -continued | |
|---|---|
| Typical serving: 25 g<br>n-3 LCPUFA content: 125 mg/serving | |
|  | [g] |
| Whole egg (liquid) | 130.0 |
| Salt | 1.0 |
| Baking agent | 2.5 |
| Cinnamon | 2.5 |
| Lemon Peel flavor | q.s. |
| Lemon Juice | q.s. |

The ROPUFA '30' n-3 Food Oil was added to the melted fat Then all other ingredients were added slowly under mixing to form a sweet short pastry.

Afterwards, the pastry was maintained at 4° C. for at least 2 hours before flattening the pastry to a thickness of about 6 mm. Pieces were cut out and brushed with egg yolk on the surface and sprinkled with cane sugar before baking.

| Parameters: | |
|---|---|
| Baking: | |
| Oven: | fan oven |
| Baking temperature: | 200° C. |
| Baking time: | 10 min. |
| Estimated baking loss 10%. | |

Example 16

Yogurt Cake

| Typical serving: 100 g<br>n-3 LCPUFA content: 250 mg/serving | |
|---|---|
|  | [g] |
| Wheat flour | 310.0 |
| Sugar incl. vanilla sugar | 240.0 |
| Whole egg (liquid) | 200.0 |
| Yogurt | 170.0 |
| Fat/Oil | 60.9 |
| Baking agent | 10.0 |
| ROPUFA '30' n-3 Food Oil | 9.1 |

ROPUFA '30' n-3 Food Oil was added to the fat/oil. The yogurt was mixed with sugar, vanilla, sugar, and eggs before addition of the fat/oil containing ROPUFA '30' n-3 Food Oil, the flour, and baking agent. The dough was beaten for at least 5 minutes at medium speed. The batter was then spread into cake tins and baked in an oven.

| Parameters: | |
|---|---|
| Baking: | |
| Oven: | fan oven |
| Baking temperature: | 190° C. |
| Baking time: | 40 min. |

Example 17

UHT Milk Drink 1.7% fat
Typical serving: 300 ml
n-3 LCPUFA content: 150 mg/serving

|  | [% wt] |
| --- | --- |
| Part I |  |
| ROPUFA '30' n-3 Food Oil | 0.200 |
| Milk 1.5% fat | 2.580 |
| Part II |  |
| Part I | 2.780 |
| Sodium ascorbate | 0.025 |
| Milk 1.5% fat | 97.195 |

Pre-emulsion

Part I was mixed together and homogenized in high pressure homogenizer ($p_1$=150 bar, $P_2$=50 bar) to reach a homogeneous emulsion.

UHT-Procedure:

Part I was added together with sodium ascorbate to the rest of the milk without incorporation of air. The mix was homogenized in a high pressure homogenizer ($p_1$=150 bar $p_2$=50 bar) and preheated in a tubular heat exchanger before thermal processing in a direct heat exchanger at 140° C. for 4 seconds, vacuum-cooling, and aseptic packaging.

Example 18

Yogurt-Set Type 3.5% fat
Typical serving: 150 g
n-3 LCPUFA content: 225 mg/serving

|  | [% wt] |
| --- | --- |
| Full fat milk (3.8% fat) | 75.0 |
| Skimmed milk (0.1% fat) | 14.9 |
| Skimmed milk powder | 2.0 |
| Sugar | 5.0 |
| Yogurt | 2.5 |
| ROPUFA '30' n-3 Food Oil | 0.6 |

The milk was heated to 35° C. before adding milk powder and sugar. This mixture was heated to 65° C. to dissolve all ingredients. ROPUFA '30' n-3 Food Oil was added to the mixture before homogenization in a high pressure homogenizer ($p_1$=150 bar, $p_2$=50 bar) at 65° C. This emulsion was then pasteurized at 80° C. for 20 minutes. After cooling to 45° C., the natural yogurt/culture was added and mixed. Then, this mixture was filled into cups and fermented at 45° C. for 34 hours, until a pH of 4.3 had been reached, and then it was stored at 4° C.

Example 19

Yogurt-Stirred Type 3.5% fat
Typical serving: 150 g
n-3 LCPUFA content: 225 mg/serving in yogurt

|  | [% wt] |
| --- | --- |
| Full fat milk (3.8% fat) | 78.8 |
| Skimmed milk (0.1% fat) | 10.8 |
| Skimmed milk powder | 2.0 |
| Stabilizer | 0.3 |
| Sugar | 5.0 |
| Yogurt | 2.5 |
| ROPUFA '30' n-3 Food Oil | 0.6 |

The milk was heated to 35° C. before adding milk powder, stabilizer, and sugar. This mixture was heated to 65° C. to dissolve all ingredients before homogenization in a high pressure homogenizer ($p_1$=150 bar, $P_2$=50 bar) at 65° C. This emulsion was then pasteurized at 80° C. for 20 minutes. After cooling to 45° C., the natural yogurt/culture was added and mixed, followed by a fermentation at 45° C. for 34 hours until a pH of 4.3 had been reached. After cooling and stirring vigorously, the yogurt was filled in cups and stored at 4° C.

Method A:

Addition of ROPUFA '30' n-3 Food Oil before homogenization:

Method B:

Addition of ROPUFA '30' n-3 Food Oil after fermentation while stirring.

The invention being thus described, it will be obvious that the same may be varied in many ways. Such variations are not to be regarded as a departure from the spirit and scope of the invention and all such modifications are intended to be included within the scope of the following claims.

We claim:

1. A process for preparing and stabilizing food-grade marine oil comprising treating marine oil with silica and vacuum steam deodorizing the marine oil at a temperature between about 140° C. and about 210° C. in the presence of 0.1%–0.4% rosemary or sage extract.

2. A process according to claim 1 wherein deodorizing is performed in the presence of rosemary extract.

3. A process according to claim 1 wherein the treating is performed in the presence of carbon.

4. A process according to claim 1 wherein the deodorizing is performed at a temperature between about 150° C. and about 190° C.

5. A process according to claim 4 wherein the deodorizing is performed at about 190° C.

6. A process according to claim 1 wherein the rosemary extract is present in an amount of about 0.2%.

7. A process according to claim 1 wherein 0.01%–0.03% ascorbyl palmitate and 0.05%–0.2% mixed tocopherol are added after deodorizing.

8. A process according to claim 7 wherein about 0.02% ascorbyl palmitate and about 0.1% mixed tocopherol are added after deodorizing.

9. A process according to claim 1 further comprising adding 0.1%–0.3% ascorbyl palmitate and 0.05%–0.2% mixed tocopherol to the marine oil.

10. A method of preparing a food product comprising adding a marine oil prepared by the process of claim 1 to a food product.

11. A method of rating the taste of an unknown marine oil comprising:

a) measuring a dynamic headspace profile of an unknown marine oil for (Z)-4-heptenal, (E)-2-hexenal, 1,5-(Z)-octadien-3-one, (E,E)-2,4-heptadienal, 3,6-nonadienal, and (E,Z)-2,6-nonadienal;

b) comparing the profile of the unknown marine oil to the following standard profile;

and c) assigning a taste factor to the unknown marine oil of from 1 to 5 based on the closest profile in the standard profile.

STANDARD PROFILE

| | | | Concentration (ppb) | | | | | | |
|---|---|---|---|---|---|---|---|---|---|
| Sample No. | Oil Type | Taste | 2,6-nonadienal | 1,5-octdien-3-one | 4-heptenal | 2-hexenal | 3,6-nonadienal | 2,4-heptadienal | Taste factor |
| 1 | EPA | Strong fish | 53 | 69 | 26 | 146 | 457 | 213 | 4 |
| 2 | EPA | Middle fish | 37 | 27 | 33 | 100 | 288 | 168 | 3 |
| 3 | EPA | Strong fish | 68 | 54 | 53 | 232 | 710 | 542 | 4 |
| 4 | EPA | No fish | 28 | 151 | 35 | 113 | 254 | 282 | 1 |
| 5 | EPA | No fish | 19 | 74 | 31 | 79 | 223 | 208 | 1 |
| 6 | EPA | Middle fish | 40 | 101 | 102 | 309 | 240 | 417 | 3 |
| 7 | EPA | No fish | 21 | 36 | 15 | 50 | 72 | 81 | 1 |
| 8 | DHA | Middle fish | 27 | 79 | 61 | 230 | 324 | 257 | 3 |
| 9 | DHA | No fish | 23 | 64 | 15 | 57 | 101 | 128 | 1 |
| 10 | EPA | No fish | 16 | 42 | 10 | 0 | 70 | 92 | 1 |
| 11 | DHA | Slight fish | 34 | 123 | 56 | 313 | 182 | 277 | 2 |
| 12 | EPA | No fish | 18 | 96 | 13 | 36 | 128 | 168 | 1 |
| 13 | DHA | No fish | 16 | 52 | 9 | 40 | 104 | 107 | 1 |
| 14 | DHA | No fish | 17 | 41 | 16 | 40 | 61 | 75 | 1 |
| 15 | DHA | Slight fish | 25 | 69 | 26 | 104 | 156 | 198 | 2 |
| 16 | EPA | Middle fish | 25 | 64 | 23 | 89 | 321 | 212 | 3 |
| 17 | EPA | No fish | 20 | 54 | 13 | 54 | 70 | 111 | 1 |
| 18 | EPA | Middle fish | 28 | 113 | 41 | 147 | 441 | 334 | 3 |
| 19 | EPA | No fish | 21 | 45 | 7 | 39 | 96 | 182 | 1 |
| 20 | EPA | Slight fish | 22 | 109 | 13 | 64 | 305 | 240 | 2 |
| 21 | EPA | No fish | 13 | 80 | 8 | 38 | 194 | 158 | 1 |
| 22 | DHA | Middle fish | 22 | 157 | 31 | 101 | 719 | 563 | 3 |
| 23 | DHA | No fish | 15 | 78 | 6 | 48 | 216 | 215 | 1 |
| 24 | EPA | No fish | 14 | 55 | 7 | 38 | 109 | 116 | 1 |
| 25 | DHA | No fish | 0 | 52 | 8 | 25 | 78 | 70 | 1 |
| 26 | DHA | Slight fish | 39 | 111 | 12 | 41 | 239 | 201 | 2 |
| 27 | DHA | No fish | 0 | 0 | 4 | 9 | 63 | 56 | 1 |
| 28 | DHA | No fish | 18 | 59 | 11 | 38 | 159 | 153 | 1 |
| 29 | EPA | Very strong fish | 646 | 587 | 1135 | 4105 | 5015 | 3690 | 5 |
| 30 | DHA | No fish | 0 | 0 | 13 | 40 | 105 | 111 | 1 |
| 31 | DHA | Slight fish | 20 | 0 | 9 | 33 | 84 | 61 | 2 |
| 32 | DHA | No fish | 0 | 71 | 7 | 32 | 164 | 129 | 1 |
| 33 | DHA | No fish | 0 | 69 | 11 | 39 | 119 | 91 | 1 |
| 34 | DHA | No fish | 0 | 76 | 7 | 51 | 177 | 123 | 1 |
| 35 | DHA | No fish | 0 | 98 | 2 | 42 | 137 | 105 | 1 |
| 36 | DHA | No fish | 13 | 34 | 6 | 32 | 44 | 34 | 1 |

* * * * *